United States Patent
Kumagai

(10) Patent No.: US 9,581,068 B2
(45) Date of Patent: Feb. 28, 2017

(54) EXHAUST GAS DILUTION DEVICE AND PM MEASUREMENT SYSTEM

(71) Applicant: HORIBA, Ltd., Kyoto (JP)

(72) Inventor: Tatsuki Kumagai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 93 days.

(21) Appl. No.: 13/958,143

(22) Filed: Aug. 2, 2013

(65) Prior Publication Data
US 2014/0036617 A1 Feb. 6, 2014

(30) Foreign Application Priority Data
Aug. 6, 2012 (JP) .................................. 2012-173896

(51) Int. Cl.
F01N 11/00 (2006.01)
G01N 1/22 (2006.01)

(52) U.S. Cl.
CPC ........... F01N 11/00 (2013.01); G01N 1/2252 (2013.01); G01N 2001/2255 (2013.01)

(58) Field of Classification Search
CPC ... F02D 41/1495; F02D 41/1456; F01N 11/00
USPC ........... 73/114.73; 60/276; 366/172.1, 173.1, 366/174.1, 175.2
See application file for complete search history.

(56) References Cited

U.S. PATENT DOCUMENTS

| 5,865,537 A * | 2/1999 | Streiff ........................ B01F 3/10 366/137 |
| 7,043,903 B2 * | 5/2006 | Onodera ............... F01N 3/0231 60/274 |
| 2002/0108451 A1 * | 8/2002 | May .......................... G01F 1/44 73/861.63 |

(Continued)

FOREIGN PATENT DOCUMENTS

| CN | 1680691 A | 10/2005 |
| CN | 1932468 A | 3/2007 |

(Continued)

OTHER PUBLICATIONS

Office Action dated Oct. 29, 2015 issued for Japanese Patent Application No. 2012-173896, pp. 1-3.

(Continued)

*Primary Examiner* — Tony G Soohoo
*Assistant Examiner* — Anshu Bhatia
(74) *Attorney, Agent, or Firm* — Brooks Kushman P.C.

(57) ABSTRACT

The present invention is one that, in measurement of exhaust gases respectively discharged from a first engine and a second engine, reduce a PM measurement error caused by sharing a dilution tunnel, and has: a dilution tunnel for diluting exhaust gas from an engine with dilution air; a diesel exhaust gas introduction path that introduces diesel exhaust gas from a diesel engine DE into the dilution tunnel; and a gasoline exhaust gas introduction path that introduces diluted gasoline exhaust gas from a gasoline engine GE into the dilution tunnel, wherein: the dilution tunnel has a gas (Continued)

mixing part that mixes the diesel exhaust gas introduced by the diesel exhaust gas introduction path and the dilution air with each other; and the gasoline exhaust gas introduction path introduces the gasoline exhaust gas into an upstream side of the gas mixing part in the dilution tunnel.

4 Claims, 3 Drawing Sheets

(56) References Cited

U.S. PATENT DOCUMENTS

| | | |
|---|---|---|
| 2004/0107762 A1* | 6/2004 | Silvis et al. ............... 73/1.06 |
| 2005/0217253 A1 | 10/2005 | Onodera et al. |
| 2007/0033996 A1 | 2/2007 | Simperl et al. |
| 2012/0036836 A1* | 2/2012 | Dickow ..................... 60/276 |

FOREIGN PATENT DOCUMENTS

| | | |
|---|---|---|
| JP | 04-071147 U | 6/1992 |
| JP | 05-006349 U | 1/1993 |
| JP | 06-294718 A | 10/1994 |
| JP | 2000-329661 A | 11/2000 |
| JP | 2000329661 | 11/2000 |
| JP | 2004-205253 A | 7/2004 |
| TW | 331528 A | 10/1995 |
| WO | 2010112286 | 10/2010 |

OTHER PUBLICATIONS

Office Action dated Nov. 2, 2016 issued for Chinese patent application No. 201310299633.2, 13 pgs.

* cited by examiner

EXHAUST GAS DILUTION DEVICE AND PM MEASUREMENT SYSTEM

CROSS-REFERENCE TO RELATED APPLICATION

This application claims priority to JP Application No. 2012-173896, filed Aug. 6, 2012, the disclosure of which is incorporated in its entirety by reference herein.

TECHNICAL FIELD

The present invention relates to an exhaust gas dilution device that dilutes exhaust gas discharged from an engine, and a PM measurement system using the exhaust gas dilution device.

BACKGROUND

As this sort of exhaust gas dilution device, as disclosed in JPA 2000-329661, as a device that measures particulate matter (PM) contained in exhaust gas discharged from an engine, there is one that has a dilution tunnel, an exhaust gas introduction pipe for introducing the exhaust gas into the dilution tunnel, and an orifice plate that is provided near an introduction port of the exhaust gas introduction pipe and formed with an orifice.

Also, as disclosed in International Publication No. WO2010/112286, there is an exhaust gas dilution device that is, by providing a single dilution tunnel with a first exhaust gas introduction pipe for introducing first exhaust gas and a second exhaust gas introduction pipe for introducing second exhaust gas, and switching between the exhaust gas introduction pipes by a switching valve, configured to be able to selectively dilute and measure any of the exhaust gases from respective engines. In addition, in the exhaust gas dilution device, on a downstream side of an orifice that mixes the first exhaust gas and dilution air with each other, the second exhaust gas introduction pipe is connected.

However, the second exhaust gas introduction pipe is connected on the downstream side of the orifice, and therefore in the case of performing PM measurement of the first exhaust gas, there is a problem that the first exhaust gas diluted by the orifice is retained in opening space of the second exhaust gas introduction pipe or attached on an inner surface forming the opening space to cause a measurement error in the PM measurement of the first exhaust gas. That is, on the downstream side of a mixing part where the first exhaust gas and the dilution gas are mixed, the exhaust gas is cooled by the dilution gas to produce PM. Further, in the case of providing the dead space on the downstream side of such a mixing part, the PM is attached in the dead space to cause the measurement error. Also, in the case of performing PM measurement of the second exhaust gas after the end of the PM measurement of the first exhaust gas, there is a problem that the PM that arises from the first exhaust and is retained or attached in the opening space of the second exhaust gas introduction pipe may be measured as PM contained in the second exhaust gas, and therefore a measurement error occurs in the PM measurement of the second exhaust gas.

SUMMARY

Technical Problem

Therefore, the present invention is made in order to solve the above problems at once, and a main intended object thereof is to, in exhaust gas measurement of exhaust gases respectively discharged from a plurality of engines, reduce an error that is caused by sharing a dilution tunnel and occurs in the exhaust gas measurement such as PM measurement.

Solution to Problem

That is, an exhaust gas dilution device according to the present invention is provided with: a dilution tunnel that is configured to be supplied with dilution air and intended to dilute exhaust gas from an engine; a first exhaust gas introduction path that is configured to introduce first exhaust gas discharged from a first engine into the dilution tunnel; and a second diluted exhaust gas introduction path that is configured to introduce second diluted exhaust gas into the dilution tunnel, the second diluted exhaust gas being gas resulting from dilution of second exhaust gas discharged from a second engine, wherein: the dilution tunnel has a gas mixing part that is configured to mix the first exhaust gas introduced by the first exhaust gas introduction path and the dilution air with each other; and the second diluted exhaust gas introduction path is configured to introduce the second diluted exhaust gas into an upstream side of the gas mixing part in the dilution tunnel.

If so, the single dilution tunnel can be used to measure the exhaust gases respectively discharged from the first engine and the second engine. This causes cost reduction and system downsizing to be achieved because, for example, in the case of performing exhaust gas measurement such as measurement of PM contained in the first exhaust gas and PM contained in the second diluted exhaust gas, it is not necessary to prepare dedicated dilution tunnels corresponding to the respective gases. Also, the second diluted exhaust gas introduction path introduces the second diluted exhaust gas into the upstream side of the gas mixing part in the dilution tunnel, and therefore in the first exhaust gas measurement, a PM measurement error occurring in the case of opening the second diluted exhaust gas introduction path on a downstream side of the gas mixing part can be reduced. For example, in the PM measurement of the first exhaust gas, the measurement error caused by retention or attachment of a measurement component of the first exhaust gas, such as PM, in opening space of the second diluted exhaust gas introduction path can be reduced. Also, in the exhaust gas measurement of the second diluted exhaust gas, such as PM measurement, the measurement component that arises from the first exhaust gas and is retained or attached in the opening space of the second diluted exhaust gas introduction path can be prevented from being measured as a measurement component contained in the second diluted gasoline exhaust gas, such as PM, and thereby an error in the exhaust gas measurement can be reduced.

In recent years, regulations on PM contained in gasoline exhaust gas discharged from a gasoline engine such as a direct injection engine has been tightened, and the PM contained in the gasoline exhaust gas has been required to be measured. In order to suitably cope with such a requirement on the basis of the present invention, it is desirable that the first engine is a diesel engine, and the second engine is a gasoline engine. If so, it is not necessary to separately prepare an exhaust gas dilution device that dilutes diesel exhaust gas discharged from the diesel engine, and an exhaust gas dilution device that dilutes gasoline exhaust gas discharged from the gasoline engine, and therefore cost reduction and system downsizing can be achieved. Further, a problem of the retention or attachment of the PM and the like in dead space due to the opening space of the second diluted exhaust gas introduction path appears more notably in the exhaust gas from the diesel engine, and therefore an effect due to not providing the dead space on the downstream side of the mixing part for the diluted exhaust gas from the diesel engine is large.

It is also possible to introduce the second diluted exhaust gas into the upstream side of the gas mixing part by opening the second diluted exhaust gas introduction path in a sidewall of the dilution tunnel; however, by doing so, the measurement component contained in the second diluted exhaust gas, such as the PM, is attached on an inner wall surface of the dilution tunnel, which becomes a factor of an error in the exhaust gas measurement such as the PM measurement. For this reason, it is desirable that the first exhaust gas introduction path and the second diluted exhaust gas introduction path join together in the dilution tunnel.

Note that there is common general technical knowledge that, in conventional PM measurement of exhaust gas, between an introduction port of an exhaust gas introduction path and a gas mixing part, a structure likely to be attached with PM is not provided. For this reason, by making the first exhaust gas introduction path and the second diluted exhaust gas introduction path join together to share an introduction port, a configuration that, between the introduction port of the second diluted exhaust gas introduction path and the gas mixing part, does not have the structure likely to be attached with PM can be realized. Accordingly, the PM contained in the second diluted exhaust gas can be prevented from being attached on the inner wall in the dilution tunnel, and thereby a measurement error can be reduced.

In the case of making the first exhaust gas introduction path and the second diluted exhaust gas introduction path join together, the measurement component attached to one of the introduction paths, such as the PM, may be included and mixed when exhaust gas is introduced from the other introduction path into the dilution tunnel, and if so, this becomes a factor of a measurement error. In order to solve this problem, it is desirable that the first exhaust gas introduction path and the second diluted exhaust gas introduction path smoothly join together so as to face in the same direction at a joining point thereof.

In order to making a configuration inside the dilution tunnel as simple as possible to prevent the attachment of the measurement component contained in each of the exhaust gases, such as the PM, it is desirable that the gas mixing part is formed of an orifice plate that is arranged with an orifice near a gas introduction port of the first exhaust gas introduction path.

Also, a PM measurement system according to the present invention is provided with: a dilution tunnel that is configured to be supplied with dilution air and intended to dilute exhaust gas from an engine; a first exhaust gas introduction path that is configured to introduce first exhaust gas discharged from a first engine into the dilution tunnel; a second diluted exhaust gas introduction path that is configured to introduce second diluted exhaust gas into the dilution tunnel, the second diluted exhaust gas being gas resulting from dilution of second exhaust gas discharged from a second engine; and a diluted exhaust gas sampling path that is provided on a downstream side in the dilution tunnel and introduces diluted exhaust gas into a PM measurement device, wherein: the dilution tunnel has a gas mixing part that is configured to mix the first exhaust gas introduced by the first exhaust gas introduction path and the dilution air with each other; and the second diluted exhaust gas introduction path is configured to introduce the second diluted exhaust gas into an upstream side of the gas mixing part in the dilution tunnel.

Advantageous Effects of Invention

According to the present invention configured as described, the single dilution tunnel can be used to measure the exhaust gases respectively discharged from the first engine and the second engine, and also the second diluted exhaust gas is prevented from being introduced into the downstream side of the gas mixing part, so that an influence of the second diluted exhaust gas introduction path on the exhaust gas measurement of the first exhaust gas, such as the PM measurement, can be reduced.

DESCRIPTION OF EMBODIMENTS

In the following, a PM measurement system using an exhaust gas dilution device according to the present invention is described with reference to the drawings.

A PM measurement system 100 of the present embodiment is one that measures particulate matter (PM) contained in diesel exhaust gas discharged from a diesel engine DE or gasoline exhaust gas discharged from a gasoline engine GE.

Figure 1:
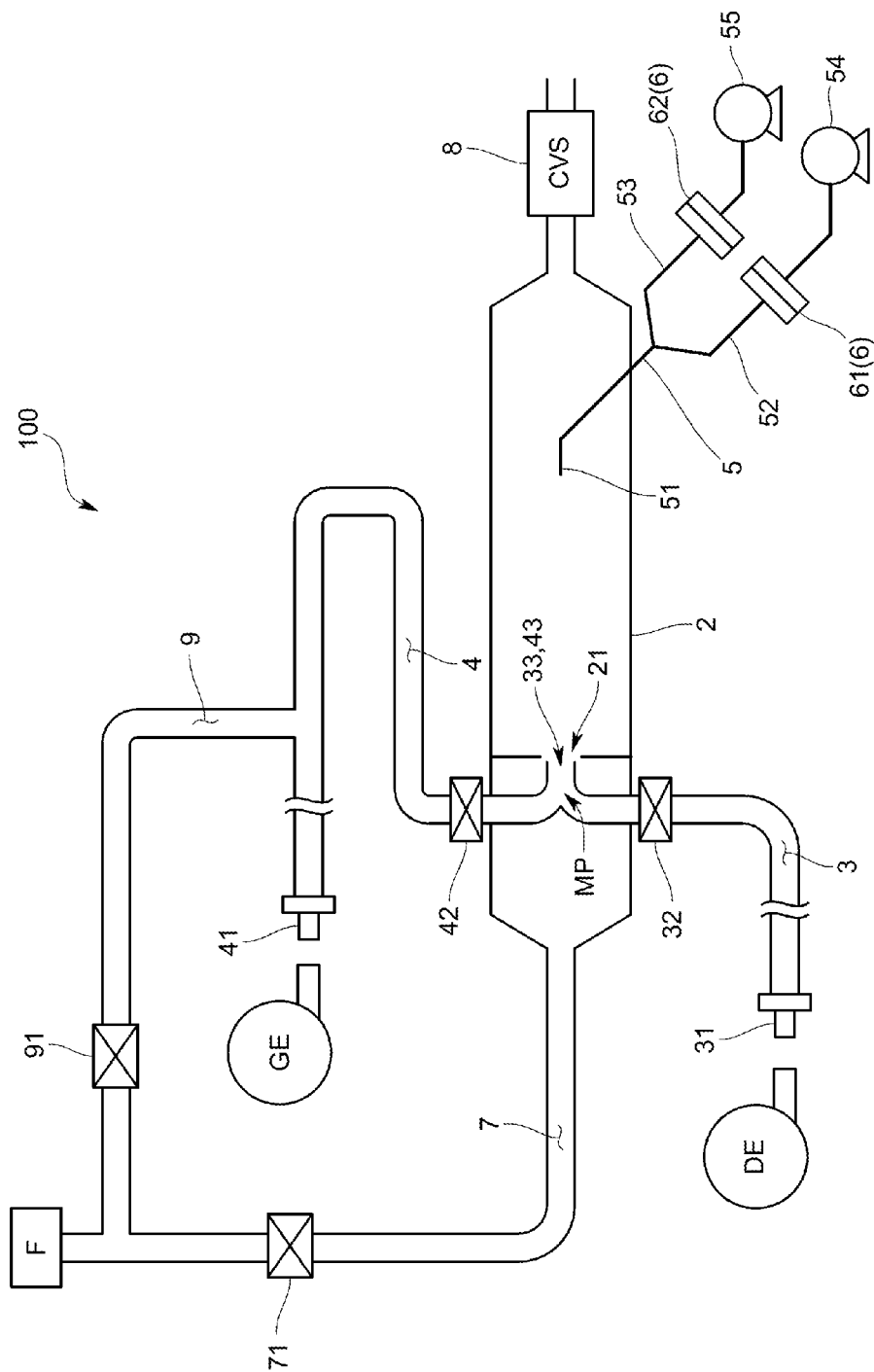
FIG. 1 is a schematic diagram of a PM measurement system using an exhaust gas dilution device of the present embodiment.

Specifically, the PM measurement system 100 is, as illustrated in FIG. 1, provided with: a dilution tunnel 2 that is supplied with dilution air and intended to dilute exhaust gas from any of the various types of engines; a first exhaust gas introduction path 3 (hereinafter referred to as a diesel exhaust gas introduction path 3) that introduces the diesel exhaust gas (first exhaust gas) from the diesel engine DE as a first engine into the dilution tunnel 2; a second diluted exhaust gas introduction path 4 (hereinafter referred to as a gasoline exhaust gas introduction path 4) that dilutes the gasoline exhaust gas from the gasoline engine GE as a second engine and introduces the diluted gasoline exhaust gas (second diluted exhaust gas) into the dilution tunnel 2; and a diluted exhaust gas sampling path 5 that is provided on a downstream side in the dilution tunnel 2 and introduces any of the diluted exhaust gases into a PM measurement device 6.

The dilution tunnel 2 is one that is formed in a substantially cylindrical shape. Also, on an upstream side in the dilution tunnel 2, a dilution air introduction path 7 for introducing the dilution air through an air cleaning filter F is connected. Also, on the downstream side in the dilution tunnel 2, a constant volume sampler (CVS) 8 including a venturi flowmeter (e.g., a critical flow venturi type (CFV)) and a suction pump is connected. In addition, the dilution air introduction path 7 is provided with an on/off valve 71 that opens/closes the dilution air introduction path 7, such as a solenoid valve.

Figure 2:
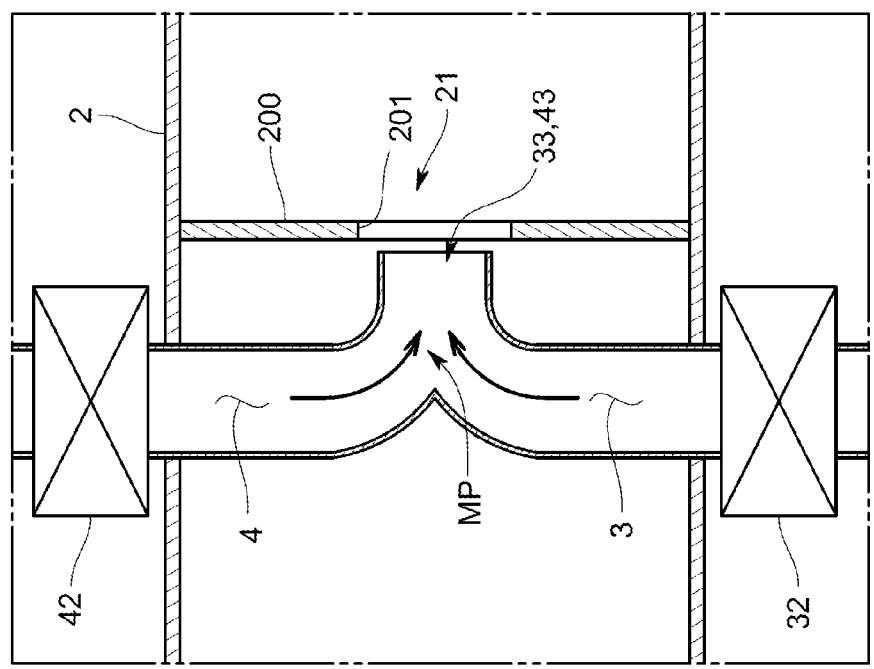
FIG. 2 is a schematic diagram illustrating a configuration near a joining point of respective exhaust gas introduction paths in the same embodiment.

Also, the inside of the dilution tunnel 2 is provided with a gas mixing part 21 that mixes the diesel exhaust gas introduced by the diesel exhaust gas introduction path 3 and the dilution air with each other. The gas mixing part 21 is, as illustrated in FIG. 2, formed of a cross-sectionally circular-shaped orifice plate 200 that is formed with an orifice 201 for narrowing down the dilution air introduced from the dilution air introduction path 7. That is, the gas mixing part 21 includes the orifice 201 and a downstream side region of the orifice 201. The orifice plate 200 is provided so as to halve the inside of the dilution tunnel 2. Also, the orifice 201 causes the dilution air introduced from the dilution air introduction path 7 to form a turbulent flow, and the dilution air is mixed with the diesel exhaust gas introduced by the diesel exhaust gas introduction path 3 or the diluted gasoline exhaust gas introduced by the gasoline exhaust gas introduction path 4.

The diesel exhaust gas introduction path 3 is one that introduces the diesel exhaust gas from an exhaust pipe connected to the diesel engine DE into the dilution tunnel 2, and at one end thereof, has a diesel exhaust gas introduction port 31 that introduces the diesel exhaust gas discharged from the exhaust pipe of the diesel engine DE. Also, on a downstream side of the diesel exhaust introduction path 3, an on/off valve 32 that opens/closes the diesel exhaust gas introduction path 3, such as a solenoid valve, is provided.

Further, an opening (diesel gas introduction port 33) at the other end of the diesel exhaust gas introduction path 3 in the dilution tunnel 2 is, as illustrated in FIG. 2, opened near the orifice 201 constituting the gas mixing part 21. That is, the orifice 201 is provided so as to be positioned near the introduction port 33 of the diesel exhaust gas introduction path 3. Specifically, the orifice 201 and the introduction port 33 are coaxially arranged, and any of the cases where the introduction port 33 is arranged near an upstream side of the orifice 201, arranged near a downstream side of the orifice 201, and arranged in the orifice 201 is possible.

The gasoline exhaust gas introduction path 4 is one that introduces the gasoline exhaust gas from an exhaust pipe connected to the gasoline engine GE into the dilution tunnel 2, and at one end thereof, has a gasoline exhaust gas introduction port 41 that introduces the gasoline exhaust gas discharged from the exhaust pipe of the gasoline engine GE.

Also, the gasoline exhaust gas introduction path 4 is connected with a dilution air introduction path 9 for diluting the gasoline exhaust gas introduced from the gasoline exhaust gas introduction port 41. As described, by in the gasoline exhaust gas introduction path 4, diluting the gasoline exhaust gas introduced into the gasoline exhaust gas introduction port 41, moisture contained in the gasoline exhaust gas is prevented from condensing in the gasoline exhaust gas introduction path 4. Further, on a downstream side of the gasoline exhaust gas introduction path 4, an on/off valve 42 that opens/closes the gasoline exhaust gas introduction path 4, such as a solenoid valve, is provided. In addition, the dilution air introduction path 9 is provided with an on/off valve 91 that opens/closes the dilution air introduction path 9, such as a solenoid valve. Also, the dilution air introduction path 7 and the dilution air introduction path 9 join together on upstream sides of the on/off valves 71 and 91, and by switching between an on/off state of the on/off valve 71 and an off/on state of the on/off valve 91, the present embodiment is configured to be able to select the introduction of the dilution air into the dilution tunnel 2 or the introduction of the dilution air into the gasoline exhaust gas introduction path 4.

Further, an opening (gasoline exhaust gas introduction port 43) at the other end of the gasoline exhaust gas introduction path 4 in the dilution tunnel 2 is opened on the upstream side of the gas mixing part 21, and the present embodiment is configured to introduce the diluted gasoline exhaust gas into the upstream side of the gas mixing par 21 of the dilution tunnel 2.

Also, by switching an on/off state of the on/off valve 32 provided in the diesel exhaust gas introduction path 3 and an off/on state of the on/off valve 42 provided in the gasoline exhaust gas introduction path 4, the present invention is configured to alternatively perform the PM measurement of the diesel exhaust gas or the PM measurement of the diluted gasoline exhaust gas.

The diluted exhaust gas sampling path 5 is one that introduces the diesel exhaust gas diluted by the dilution tunnel 2 or the diluted gasoline exhaust gas into the PM measurement device 6. The diluted exhaust gas sampling path 5 of the present embodiment has, at one end thereof, a sampling port 51 that is opened on the downstream side of the gas mixing part 21 in the dilution tunnel 2, and the other end thereof is branched into two branched paths 52 and 53, which are respectively provided with filters 61 and 62 (PM measurement devices 6) for collecting PM contained in any of the diluted exhaust gases. One 52 of the branched paths forms a sample gas flow path for flowing sample gas (gas collected through the sampling port 51) at the time of collecting the PM (at the time of measuring the exhaust gas), and the other branched path 53 forms a bypass flow path for flowing the sample gas at the time of not collecting the PM (at the time of reference measurement). Further, at downstream ends of the respective branched paths 52 and 53, suction pumps (e.g., roots blower pumps) 54 and 55 of which suction capabilities can be varied by rotating speed control are provided.

The suction pump 54 or 55 is adapted to, by being controlled by an unillustrated control device (PID controller), make a flow rate of gas passing through the filter 61 follow a gas flow rate in the dilution tunnel 2 with constantly keeping a constant proportional relationship between the gas flow rates. That is, the gas flow rate measured by an unillustrated flowmeter provided on a downstream side of the diluted exhaust sampling path 5 is subjected to flow rate control with having the constant proportional relationship with the gas flow rate measured by the constant volume sampler (CVS) 8.

Also, as illustrated in FIG. 2, the diesel exhaust gas introduction path 3 and the gasoline exhaust gas introduction path 4 join together in the dilution tunnel 2, and the introduction port 33 of the diesel exhaust gas introduction path 3 and the introduction port 43 of the gasoline exhaust gas introduction path 4 are configured to be a shared opening.

Specifically, a downstream side of a joining point MP of the respective exhaust gas introduction paths 3 and 4 is configured to be a linearly-shaped shared flow path. Also, upstream sides of the joining point MP in the respective exhaust gas introduction paths 3 and 4 substantially vertically penetrate through a sidewall of the dilution tunnel 2, and are formed in curved shapes from sidewall sides of the dilution tunnel 2 to the joining point MP, respectively. Further, the two exhaust gas introduction paths 3 and 4 are configured to smoothly join together so as to face in the same direction toward the joining point MP. Specifically, one of the two exhaust gas introduction paths is configured to join the other exhaust gas introduction path so as to face in a tangential direction of the other exhaust gas introduction path. In doing so, in the case of making the diesel exhaust gas introduction path 3 and the gasoline exhaust gas introduction path 4 join together, and introducing exhaust gas from one of the introduction paths into the dilution tunnel 2, PM attached on an inner surface of the other introduction path is prevented from being included and mixed.

Also, in the present embodiment, the two exhaust gas introduction paths 3 and 4 are configured to have symmetrical shapes in the dilution tunnel 2, respectively, and specifically configured to be symmetrical to a central axis (axis passing through the opening center of the orifice 201) of the dilution tunnel 2. In doing so, the diesel exhaust gas introduction path 3 and the gasoline exhaust gas introduction path 4 are connected to the sidewall at positions facing to each other in the dilution tunnel 2, and therefore piping outside the dilution tunnel 2 can be facilitated.

According to the PM measurement system 100 according to the present embodiment configured as described, the single dilution tunnel 2 can be used to measure the exhaust gases respectively discharged from the diesel engine DE and the gasoline engine GE. This causes cost reduction and system downsizing to be achieved because, for example, in the case of measuring the PM contained in the gasoline exhaust gas and the PM contained in the diesel exhaust gas, it is not necessary to prepare dedicated dilution tunnels corresponding to the respective gases.

Also, the gasoline exhaust gas introduction path 4 introduces the diluted gasoline exhaust gas into the upstream side of the gas mixing part 21 in the dilution tunnel 2, and therefore in the diesel exhaust gas measurement, a PM measurement error occurring in the case of opening the gasoline exhaust gas introduction path 4 on the downstream side of the gas mixing part 21 can be reduced. For example, in the PM measurement of the diesel exhaust gas, the measurement error caused by retention or attachment of the PM of the diesel exhaust gas in the opening space of the gasoline exhaust gas introduction path 4 can be reduced. Also, in the PM measurement of the diluted gasoline exhaust gas, the PM that arises from the diesel exhaust gas and is retained or attached in the opening space of the gasoline exhaust gas introduction path 4 can be prevented from being measured as the PM contained in the diluted gasoline exhaust gas, and thereby a measurement error can be reduced.

The diesel exhaust gas introduction path 3 and the gasoline exhaust gas introduction path 4 join together in the dilution tunnel 2, and therefore the introduction port 43 of the gasoline exhaust gas introduction path 4 and the introduction port 33 of the diesel exhaust gas introduction path 3 can be shared by each other. In doing so, the PM contained in the diluted gasoline exhaust gas can be prevented from being attached on an inner wall on the upstream side of the gas mixing part 21 inside the dilution tunnel 2, and thereby a measurement error can be reduced. Also, by making the two exhaust gas introduction paths 3 and 4 join together in the dilution tunnel 2, a shared path part can be made as short as possible, and therefore mutual interference between the PM and the PM respectively contained in the various types of gases can be prevented.

Note that the present invention is not limited to the above-described embodiment.

Figure 3:
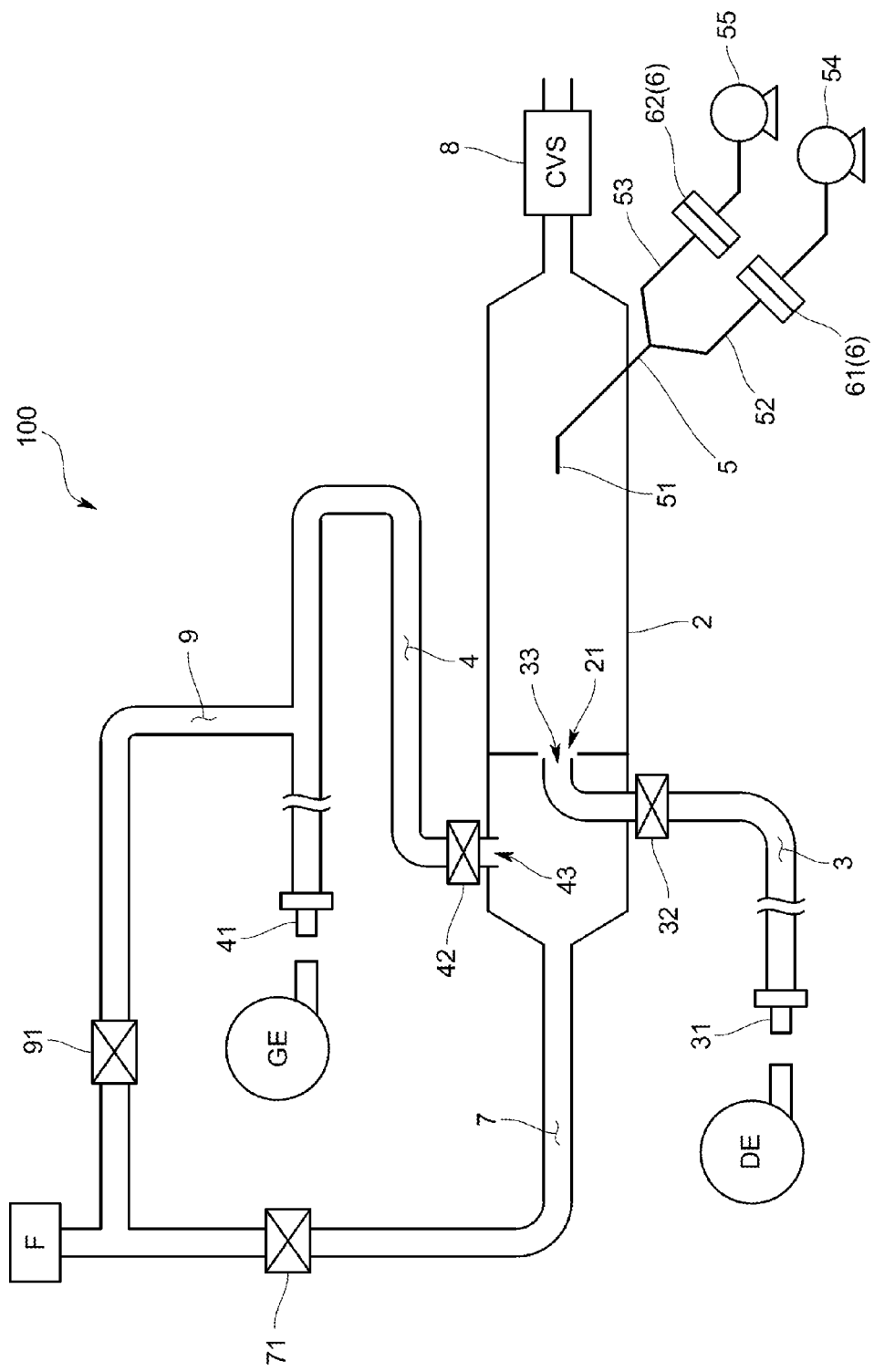
FIG. 3 is a schematic diagram of a PM measurement system using an exhaust gas dilution device of a variation.

For example, the above-described embodiment is one in which the two exhaust gas introduction paths 3 and 4 join together in the dilution tunnel 2; however, the present invention may be configured to, in the dilution tunnel 2, open the gasoline exhaust gas introduction path 4 at a position different from an opening position of the diesel exhaust gas introduction path 3, or as illustrated in FIG. 3, configured to open them in the sidewall of the dilution tunnel 2. Besides, the present invention may be configured to make the two exhaust gas introduction paths 3 and 4 join together outside the dilution tunnel 2, and introduce a combined path resulting from the joining into the dilution tunnel.

Also, in the above-described embodiment, described is a configuration in which the one dilution tunnel 2 is provided with the two exhaust gas introduction paths 3 and 4; however, the present invention may be adapted to provide three or more exhaust gas introduction paths. For example, the present invention may be one that is provide with two diesel exhaust gas introduction paths 3 and one gasoline exhaust gas introduction path 4. That is, in the case of using one dilution tunnel to dilute first exhaust gas from a plurality of first engines, a plurality of first exhaust gas introduction paths respectively corresponding to the plurality of first engines may be provided to connect the plurality of first exhaust gas introduction paths to the dilution tunnel. Alternatively, in the case of using one dilution tunnel to dilute second diluted exhaust gas from a plurality of second engines, a plurality of second diluted exhaust gas introduction paths respectively corresponding to the plurality of second engines may be provided to connect the plurality of second diluted exhaust gas introduction paths to the dilution tunnel.

Further, in the above-described embodiment, described is the case where the first engine is the diesel engine, and the second engine is the gasoline engine; however, both of the first and second engines may be diesel engines, or gasoline engines.

Still further, in the above-described embodiment, the diesel exhaust gas introduction path 3 and the gasoline exhaust gas introduction path 4 are connected to the dilution tunnel 2 so as to face to each other; however, both of the exhaust gas introduction paths 3 and 4 may be connected to the dilution tunnel 2 from the same direction. In doing so, the two exhaust gas introduction paths join together with facing in the same direction, and therefore when exhaust gas is introduced from one of the introduction paths into the dilution tunnel 2, PM attached on an inner surface of the other introduction path can be further prevented from being included and mixed.

In addition, the gasoline exhaust gas introduction path (second diluted exhaust gas introduction path) in the above-described embodiment is one that is connected with the dilution air introduction path for diluting the gasoline exhaust gas, and dilutes the gasoline exhaust gas in the second diluted exhaust gas introduction path; however, besides, the gasoline exhaust gas introduction path may be one that receives gasoline exhaust gas diluted by a separately provided dilution device, and introduces the diluted exhaust gas into the dilution tunnel.

Besides, it should be appreciated that the present invention is not limited to the above-described embodiment, but can be variously modified without departing from the scope thereof.

REFERENCE SIGNS LIST

100: PM measurement system

DE: Diesel engine (first engine)

GE: Gasoline engine (second engine)

2: Dilution tunnel

21: Gas mixing part

3: Diesel exhaust gas introduction path (first exhaust gas introduction path)

4: Gasoline exhaust gas introduction path (second diluted exhaust gas introduction path)
MP: Joining point
5: Diluted exhaust gas sampling path
6: PM measurement device

What is claimed is:

1. An exhaust gas dilution device comprising:
a dilution tunnel configured to be supplied with dilution air;
a first exhaust gas introduction path configured to introduce into the dilution tunnel first exhaust gas discharged from a first engine; and
a second diluted exhaust gas introduction path configured to introduce into the dilution tunnel second diluted exhaust gas that results from dilution of second exhaust gas discharged from a second engine, wherein
the dilution tunnel contains and surrounds a gas mixing part configured to mix the dilution air and the first exhaust gas, and
the first exhaust gas introduction path and the second diluted exhaust gas introduction path each extend into an interior of the dilution tunnel, and physically merge so the first exhaust gas introduction path and the second gas introduction path generally face a same direction at a common joint to form a common outlet (i) that extends from the common joint such that the first exhaust gas introduction path and the second diluted exhaust gas introduction path each branch from the common outlet, (ii) inside the dilution tunnel such that the dilution tunnel surrounds the common outlet, and (iii) configured to direct the first exhaust gas and the second diluted exhaust gas toward an upstream side of the gas mixing part.

2. The exhaust gas dilution device according to claim 1, wherein the gas mixing part includes an orifice plate arranged with an orifice near the common outlet.

3. A particulate matter measurement system comprising:
a dilution tunnel configured to be supplied with dilution air;
a first exhaust gas introduction path configured to introduce into the dilution tunnel first exhaust gas discharged from a first engine;
a second diluted exhaust gas introduction path configured to introduce into the dilution tunnel second diluted exhaust gas that results from dilution of second exhaust gas discharged from a second engine; and
a diluted exhaust gas sampling path provided on a downstream side of the dilution tunnel, and configured to introduce diluted exhaust gas into a particulate matter measurement device, wherein
the dilution tunnel contains and surrounds a gas mixing part configured to mix the dilution air and the first exhaust gas, and
the first exhaust gas introduction path and the second diluted exhaust gas introduction path each extend into an interior of the dilution tunnel, and physically merge to form a common outlet (i) inside the dilution tunnel such that the dilution tunnel surrounds the common outlet and (ii) configured to direct the first exhaust gas and the second diluted exhaust gas toward an upstream side of the gas mixing part.

4. An exhaust gas dilution device comprising:
a dilution tunnel configured to be supplied with dilution air;
a first exhaust gas introduction path extending into the dilution tunnel, and defining a first outlet disposed inside the dilution tunnel configured to introduce into the dilution tunnel first exhaust gas discharged from a first engine; and
a second diluted exhaust gas introduction path extending into the dilution tunnel, and defining a second outlet disposed in the dilution tunnel configured to introduce into the dilution tunnel second diluted exhaust gas that results from dilution of second exhaust gas discharged from a second engine, wherein
the dilution tunnel contains and surrounds a gas mixing part including an orifice and configured to mix the dilution air and the first exhaust gas,
the second outlet is disposed upstream of the gas mixing part, and
a location of the first outlet is spaced away downstream from a location of the second outlet.

* * * * *